United States Patent [19]

Dingwall et al.

[11] 4,205,977
[45] Jun. 3, 1980

[54] AGENT AND METHOD FOR INFLUENCING PLANT GROWTH

[75] Inventors: John G. Dingwall, Sale; Eric K. Baylis, Stockport, both of England; Colin D. Campbell, Beith, Scotland

[73] Assignee: CIBA-GEIGY Corporation, Ardsley, N.Y.

[21] Appl. No.: 960,357

[22] Filed: Nov. 13, 1978

[30] Foreign Application Priority Data

Nov. 19, 1977 [GB] United Kingdom ............... 48265/77

[51] Int. Cl.² .................................................. A01N 5/00
[52] U.S. Cl. ............................................... 71/76; 71/86; 260/502.5
[58] Field of Search ....................................... 71/86, 76

[56] References Cited

U.S. PATENT DOCUMENTS

| | | | |
|---|---|---|---|
| 3,160,632 | 12/1964 | Fon Toy et al. | 424/211 |
| 3,501,556 | 3/1970 | Weil et al. | 71/86 |
| 3,764,677 | 10/1973 | Kerst et al. | 71/86 |
| 3,894,861 | 7/1975 | Hartman | 71/86 |
| 4,120,688 | 10/1978 | Otten | 71/86 |
| 4,127,401 | 11/1978 | Cöln et al. | 71/86 |

FOREIGN PATENT DOCUMENTS

50-101536 8/1975 Japan ............................. 71/86

OTHER PUBLICATIONS

Greenham, "Studies on Phytocides", (1957), Aust. J. Biol. Sci., 10, pp. 180-188, (1957).
Gutman et al., "(O-carbamoyl oxime) phosphate, etc"; (1968), CA 71, No. 30236q., (1969).

Primary Examiner—Glennon H. Hollrah
Attorney, Agent, or Firm—Harry Falber

[57] ABSTRACT

Agent for influencing plant growth, in particular a herbicidal and plant growth-inhibiting agent containing in addition to carriers and/or other additives, at least one compound of the formula:

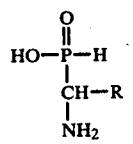

I in which R is hydrogen an alkyl group having from 1 to 5C atoms, which is unsubstituted or substituted by hydroxyl, salts thereof with either strong monobasic or polybasic acids or with inorganic or organic bases, or optical isomers thereof, as the active component.

9 Claims, No Drawings

AGENT AND METHOD FOR INFLUENCING PLANT GROWTH

The invention relates to a novel agent for influencing plant growth, in particular a herbicidal and plant growth-inhibiting agent, and to a method for inhibiting and suppressing plant growth in monocotyledonous and dicotyledonous plants, especially grasses, cereal crops, soya, tobacco and ornamental plants.

The agent, according to the invention, for influencing plant growth, in particular a herbicidal and plant growth-inhibiting agent, contains, in addition to carriers and/or other additives, at least one α-aminoalkanephosphonous acid derivative of the formula I

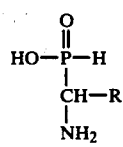

in which R is hydrogen or an alkyl group having 1 to 5 C atoms, which is unsubstituted or substituted by hydroxyl, salts thereof with either strong monobasic or polybasic acids or with inorganic or organic bases, or optical isomers thereof, as the active component.

Strong acids are to be understood as meaning, in principle, all those strong acids which are capable of forming salts with the amino group of the molecule and which are physiologically acceptable to plants.

Inorganic and organic bases are to be understood as meaning, in principle, all those inorganic and organic bases which are capable of forming salts with the acidic hydroxyl group of the molecule and which are physiologically acceptable to plants.

Alkyl groups R can be straight-chain or branched. Examples of alkyl groups according to the definition are the methyl, ethyl, n-propyl, isopropyl, n-butyl, sec.-butyl, tert.-butyl, n-pentyl, hydroxymethyl and α-hydroxyethyl groups. R is preferably hydrogen or an unsubstituted straight-chain alkyl group having 1–5 C atoms, and in particular the methyl group.

The compounds of the formula I wherein R is optionally substituted alkyl are known and have been described, together with their manner of preparation, in German OS No. 2,722,162 and Belgium Pat. No. 854,843. The compound of formula I wherein R is hydrogen (aminomethan phosphonous acid) has been described in U.S. Pat. No. 3,160,632.

The compounds of the formula I can be prepared, for example, by reacting a compound of the formula II

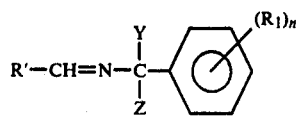

in which R' is optionally substituted alkyl, Y is hydrogen or a group of the formula III

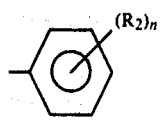

and Z is hydrogen, methyl or a group of the formula IV

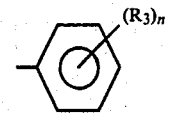

in which $R_1$, $R_2$ and $R_3$ independently of one another are halogen, for example chlorine or bromine, alkyl or alkoxy having 1–3 C atoms and n is 0, 1 or 2, with hypophosphorous acid, a N-substituted α-aminophosphonous acid of the formula V

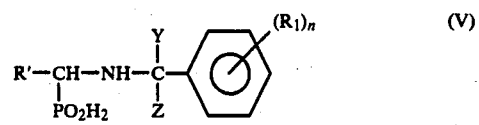

in which R', $R_1$, Y, Z and n are as defined above, being obtained, which is converted into a compound of the formula I by acid cleavage. The strong acid present is then removed. If desired, the acid cleavage can be carried out in the presence of a compound which reacts readily with a carbonium ion. Protective groups which may be present on the substituent R can be removed at any time, i.e. before, during or after the reaction. n is preferably 0, but if n is 1 or 2, $R_1$, $R_2$ and $R_3$ preferably have the same meaning.

Examples of suitable strong acids for the acid cleavage are hydrogen halide acids and carboxylic acids, such as trifluoroacetic acid or hydrobromic acid. The resulting compounds can be obtained in the free form by applying methods which are customary for amino acids, for example the method using ion exchangers or propyleneoxide.

The Schiff's bases of the general formula II can be prepared by reacting aldehydes of the formula VI

with an amine of the formula VII

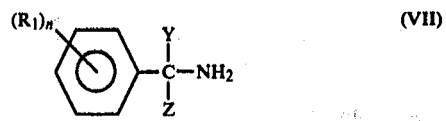

in which R', $R_1$, Y, Z and n are as defined above.

Compounds of the formula I can also be obtained by reacting an aldehyde of the formula VI with a salt of the formula VIII

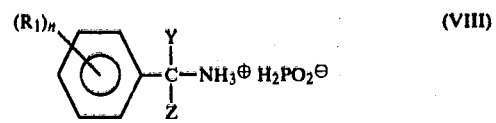

in which $R_1$, Y, Z and n are as defined above, and converting the resulting N-substituted α-aminophosphonous acid of the formula V into a compound of the formula I by acid cleavage. The acid present is then removed.

Depending on the process conditions and starting materials, the active compounds of the formula I are obtained in the free form or in the form of their salts with acids or bases. Salts with monobasic or polybasic acids can be prepared, for example, using hydrogen halide acids or aliphatic or aromatic carboxylic and sulphonic acids, such as formic, acetic and propionic acid, chloroacetic acid, methanesulphonic and ethanesulphonic acid as well as p-toluenesulphonic acid. Salts with bases can be prepared, for example, using alkali metal hydroxides and alkaline earth metal hydroxides, such as lithium hydroxide, potassium hydroxide, sodium hydroxide, calcium hydroxide and magnesium hydroxide, or alkylamines, such as isopropylamine, β-hydroxyethylamine and diethanolamine.

Depending on the meaning of R, (other than when R is hydrogen) there can be at least one optically active centre in the compounds according to the invention.

Depending on the number of asymmetric C atoms and the choice of starting materials and procedures, the active compounds of the formula I can be in the form of diasteriomeric or racemic mixtures, in the form of racemates or in the form of optical antipodes.

Diasteriomeric or racemic mixtures can be separated into the pure diasteriomers or racemates in a known manner on the basis of the physico-chemical differences of the constituents, for example by chromatography and/or fractional crystallisation, and can then be resolved into the corresponding antipodes.

The agents according to the invention are prepared in a manner which is in itself known by intimate mixing and grinding of active compounds of the formula I with suitable carriers, if desired with addition of dispersing agents or solvents which are inert towards the active compounds. The active compounds may exist, and be used, in the following processing forms:

Solid processing forms: dusting agents, sprinkling agents, granules, coated granules, impregnated granules and homogeneous granules;

Active compound concentrates which are dispersible in water: wettable powders, pastes and emulsions:

Liquid processing forms: solutions.

In order to prepare solid processing forms (dusting agents, sprinkling agents and granules), the active compounds are mixed with solid carriers. Examples of carriers which can be used are kaolin, talc, bolus, loess, chalk, limestone, lime grits, attapulgite, dolomite, diatomaceous earth, precipitated silica, alkaline earth metal silicates, sodium and potassium aluminosilicates (feldspars and micas), calcium and magnesium sulphates, magnesium oxide, ground plastics, fertilisers, such as ammonium sulphate, ammonium phosphate, ammonium nitrate and urea, ground vegetable products, such as cereal flour, bark flour, wood flour, nutshell flour, cellulose powder, plant extract residues, active charcoal and the like, in each case on their own or as mixtures with one another.

Granules can be prepared by, for example, dissolving the active compounds in an organic solvent, applying the solution thus obtained to a granulated material, for example attapulgite, silica, granicalcium or bentonite, and then again evaporating the organic solvent.

It is also possible to prepare polymer granules by, for example, impregnating finished, porous polymer granules such as urea/formaldehyde polymers, polyacrylonitrile and polyesters, having a specific surface area and an advantageous predetermined absorption/desorption ratio, with the active compounds, for example in the form of their solutions (in a low-boiling solvent) and removing the solvent. Such polymer granules can be applied in the form of micro-granules with bulk densities of, preferably, 300 g/liter, also with the aid of atomisers. Atomising can be effected over extensive treatment areas by means of aircraft.

Granules can also be obtained by compacting the carrier with the active compounds and additives and then comminuting the mixture.

Furthermore, it is possible to add to these agents additives which stabilise the active compound and/or non-ionic, anionic and cationic materials which, for example, improve the adhesion of the active compounds to plants and parts of plants (adhesives and glues) and/or ensure better wettability (wetting agents) and dispersibility (dispersing agents). It is possible to use, for example, the following materials as adhesives: olein/lime mixture, cellulose derivatives (methylcellulose and carboxymethylcellulose), hydroxyethylene glycol ethers of monoalkylphenols and dialkylphenols having 5 to 15 ethylene oxide residues per molecule and 8 to 9 carbon atoms in the alkyl radical, ligninsulphonic acid, its alkali metal salts and alkaline earth metal salts, polyethylene glycol ethers ("Carbowaxes"), fatty alcohol polyglycol ethers having 5 and 20 ethylene oxide residues per molecule and 8 to 18 carbon atoms in the fatty alcohol part, condensation products of ethylene oxide and propylene oxide, polyvinylpyrrolidones, polyvinyl alcohols, condensation products of urea/formaldehyde and latex products.

Water-dispersible active compound concentrates, i.e. wettable powders, pastes and emulsion concentrates, are agents which can be diluted with water to any desired concentration. They consist of active compound, carrier, if desired additives which stabilise the active compound, surface-active substances and anti-foaming agents and, if desired, solvents.

The wettable powders and pastes are obtained by mixing and grinding the active compounds with dispersing agents and pulverulent carriers in suitable devices until homogeneity is achieved. Examples of carriers are those mentioned above for the solid processing forms. In some cases it is advantageous to use mixtures of different carriers. Examples of dispersing agents which can be used are: condensation products of sulphonated naphthalene and sulphonated naphthalene derivatives with formaldehyde, condensation products of naphthalene or of naphthalenesulphonic acids with phenol and formaldehyde, and alkali metal salts, ammonium salts and alkaline earth metal salts of ligninsulphonic acid, as well as alkylarylsulphonates, alkali metal salts and alkaline earth metal salts of dibutylnaphthalenesulphonic acid, fatty alcohol sulphates, such as salts of sulphated hexadecanols and heptadecanols, and salts of sulphated fatty alcohol polyethylene glycol ethers, the sodium salt of oleyl methyl tauride, di-tertiary acetylene glycols, dialkyldilaurylammonium chloride and alkali metal salts and alkaline earth metal salts of fatty acids.

Examples of anti-foaming agents which can be used are silicones.

The active compounds are mixed, ground, sieved and strained with the above mentioned additives, in such a way that the particle size of the solid component does not exceed 0.02 to 0.04 mm in the case of wettable powders and 0.03 mm in the case of pastes. To prepare emulsion concentrates and pastes, dispersing agents, such as have been listed in the preceding sections, organic solvents and water are used. Examples of suitable solvents are the following: alcohols, benzene, xylenes, toluene, dimethylsulphoxide, N,N-dialkylated amides and trialkylamines. The solvents must be virtually odourless and inert towards the active compounds and should not be readily combustible.

Furthermore, the agents according to the invention can be used in the form of solutions. For this purpose, the active compound or several active compounds of the formula I is/are dissolved in suitable organic solvents, solvent mixtures, water or mixtures of organic solvents with water.

The content of active compound in the agents described above is between 0.1 and 95%, preferably between 1 and 80%.

Use forms can be diluted down to 0.001%. The amounts used are as a rule 0.1 to 10 kg of active substance/hectare, preferably 0.25 to 5 kg of active substance/hectare. The active compounds of the formula I can be formulated, for example, as follows (parts are parts by weight):

DUSTING AGENTS

The following substances are used for the preparation of (a) a 5% strength dusting agent and (b) a 2% strength dusting agent:
(a) 5 parts of D,L-1-aminoethanephosphonous acid and 95 parts of talc,
(b) 2 parts of D,L-1-amino-n-butanephosphonous acid, 1 parts of highly disperse silica and 97 parts of talc.

The active compounds are mixed and ground with the carriers.

GRANULES

The following substances are used for the preparation of 5% strength granules:
5 parts of D,L-1-amino-2-methylpropanephosphonous acid,
0.25 part of epichlorohydrin,
0.25 part of cetylpolyethylene glycol ether containing 8 mols of ethylene oxide,
3.50 parts of polyethylene glycol and 91 parts of kaolin (particle size 0.3 to 0.8 mm).

The active substance is mixed with the epichlorohydrin and dissolved in acetone, after which polyethylene glycol and cetyl polyethylene glycol ether are added. The solution thus obtained is sprayed onto kaolin and the acetone is subsequently evaporated off in vacuo.

WETTABLE POWDERS

The following constituents are used for the preparation of (a) a 50% strength wettable powder, (b) a 25% strength wettable powder and (c) a 10% strength wettable powder:

(a) 50 parts of D,L-1-amino-n-pentanephosphonous acid 5 parts of sodium dibutylnaphthylsulphonate,
3 parts of a naphthalenesulphonic acids/phenolsulphonic acids/formaldehyde condensate, 3:2:1,
20 parts of kaolin and
22 parts of Champagne chalk;

(b) 25 parts of the diethanolamine salt of the above active compound 5 parts of the sodium salt of oleylmethytauride,
2.5 parts of a naphthalenesulphonic acids/formaldehyde condensate,
0.5 part of carboxymethylcellulose,
5 parts of neutral potassium aluminium silicate and
62 parts of kaolin;

(c) 10 parts of (−)-1-aminoethanephosphonous acid 3 parts of mixture of the sodium salts of saturated fatty alcohol sulphates,
5 parts of a naphthalenesulphonic acids/formaldehyde condensate and
82 parts of kaolin.

The active compound indicated is absorbed onto the appropriate carriers (kaolin and chalk) and is then mixed and ground. Wettable powders of excellent wettability and suspensibility are obtained. Suspensions of any desired active compound concentration can be obtained from such wettable powders by dilution with water. Suspensions of this type are used for combating weeds and wild grasses in crops of plants by the pre-emergence process, and for the treatment of lawns.

PASTE

The following substances are used for the preparation of a 45% strength paste:
45 parts of D,L-1-amino-n-butanephosphonous acid,
5 parts of sodium aluminium silicate,
14 parts of cetyl polyethylene glycol ether containing 8 moles of ethylene oxide,
1 part of oleyl polyethylene glycol ether containing 5 mols of ethylene oxide,
2 parts of spindle oil,
23 parts of water and
10 parts of polyethylene glycol.

The active compound is intimately mixed and ground with the additives in apparatus which is suitable for this purpose. A paste is obtained, from which suspensions of any desired concentration can be prepared by dilution with water. The suspensions are suitable for the treatment of lawns.

EMULSION CONCENTRATE

For the preparation of a 25% strength emulsion concentrate,
25 parts of D,L-1-aminoethanephosphonous acid,
5 parts of a mixture of nonylphenol polyoxyethylene and calcium dodecylbenzenesulphonate,
35 parts of 3,5,5-trimethyl-2-cyclohexene-1-one and
35 parts of dimethylformamide,
are mixed with one another. This concentrate can be diluted with water to give emulsions of suitable concentrations.

Instead of the particular active compound indicated in the above formulation examples, it is also possible to use other compounds from amongst those included in the formula I.

The active compounds contained in the agents according to the invention influence the plant growth in various ways. Thus they inhibit, delay or suppress, in particular, the growth and germination. They therefore have a post-emergent herbicidal action as well as a growth inhibiting action.

Agents according to the invention, which contain at least one compound of the formula I as the active component, are suitable, in particular, for inhibiting and suppressing plant growth in monocotyledonous and dicotyledonous plants by post-emergent treatment of the sown areas or of the plants, such as shrubs, trees, leguminous crops, sugar cane, onion and potato tubers, fruit trees and vines and, in particular, grasses, cereal crops, tobacco, soya and ornamental plants.

The action achieved, in particular, by the active compounds of the formula I is the desired reduction in plant size, especially the height of growth. In general, a certain change in the form of the plant is associated with this. In direct association with the reduction of the height of growth, the plant is strengthened. The leaves and stem develop more strongly. The resistance to kinking of monocotyledonous plants is increased by shortening the internodal distances. Crop losses due to a thunderstorm, continuous rain and the like, which usually lead to lodging of cereal crops and leguminous crops, can be largely prevented in this manner and harvesting can thus be made easier. As a side effect, reduced height of growth of useful plants leads to a saving of fertilisers. This also applies, in the same way, to ornamental plants, ornamental lawns, sports fields or other grassed areas.

However, one of the most important problems of pure grass plantings is the actual cutting of the grass, whether in public parks in urban areas, on industrial sites, on playing fields or alongside motor-roads, aircraft landing strips, railway embankments or the sloping banks of waterways. In all these cases it is necessary to mow the lawn or cut the growth of grass periodically. This is not only very expensive in terms of labour and machinery, but, in the transport sector, also involves considerable dangers for the personnel concerned and for the occupants of vehicles.

There is therefore, particularly in areas with large traffic networks, an urgent need on the one hand to maintain and care for the greensward which is necessary to strengthen road verges and embankments on traffic routes and, on the other hand, to keep it at a medium height of growth during the whole vegetation period, using simple measures. This need is met in a very favourable manner by applying active compounds of the formula I.

By treating trees, shrubs and hedges, in particular in urban and industrial areas, with compounds of the formula I, the labour-intensive mowing work can be reduced in an analogous manner.

The growth of shoots and/or the fertility of fruit trees and vines can also be advantageously influenced by using the active compounds of the formula I.

Ornamental plants with pronounced longitudinal growth can be grown as compact pot plants by treatment with the active compounds mentioned.

The active compounds of the formula I are also used for inhibiting the growth of undesired side shoots, for example in tobacco and ornamental plants, whereby the labour-intensive manual breaking off of these shoots is avoided, and furthermore for the inhibition of sprouting in the case of stored tubers, for example in the case of tubers of ornamental plants and in the case of onions and potatoes, and finally for increasing the yield in the case of crop plants having an intense vegetative growth, such as soya and sugar cane, by accelerating the transition from the vegetative growth phase to the generative growth phase through application of active compounds of the formula I.

The active compounds of the formula I are preferably employed for inhibiting the growth of grasses, especially perennial grasses, such as *Cyperus species* and the like, and of cereal crops, tobacco, soya and ornamental plants.

The amounts used vary and depend on the time of application. In general, they are between 0.1 and 5 kg of active compound per hectare for the treatment of existing crops, preferably up to 4 kg per hectare.

The action of the active compounds according to the definition is directed towards the parts of the plant which are above ground (contact action), in particular the leaves.

The action as a powerful growth inhibitor is shown by the fact that most of the species of plants treated in a post-emergent manner stop growing after an experimental period of three weeks, the parts of the plant treated assuming a dark-green coloration. However, the leaves do not fall.

In the case of some species of plants, this growth inhibition already occurs at a dosage of 0.5 kg/hectare and less.

Since not all species of plants are equally powerfully inhibited, it is possible to use the active compounds selectively when a particular low dosage is chosen.

The active compounds of the formula I are also interesting combination partners for a number of herbicides of the diphenyl ether, phenylurea and triazine series for use on cereal crops, maize and sugar cane and in fruit growing and viticulture.

In areas with an increased danger of erosion, the active compounds of the formula I can be used as growth inhibitors on the most diverse crops.

In this case, the weed cover is not removed but only inhibited to such an extent that it can no longer compete with the crop plants.

The following Examples further illustrate the present invention.

USE EXAMPLES 1 to 3

The following test methods were used to demonstrate the usefulness of the active compounds as herbicides (post-emergent) and as growth inhibitors:

USE EXAMPLE 1

Post-emergent herbicidal action (contact herbicide)

The plants of 7 weeds and crop plants, both monocotyledonous and dicotyledonous, were sprayed after emergence (in the 4-leaf to 6-leaf stage) with an aqueous active compound formulation in a dosage of 4 kg of active substance per hectare, and the plants were kept at 24°–26° C. and a relative atmospheric humidity of 45–60%. The test was evaluated 5 days and 15 days after treatment and the result is given in Table I.

TABLE 1

| | POST-EMERGENT HERBICIDAL ACTION | | | | | | |
|---|---|---|---|---|---|---|---|
| Plant<br>Compound | Avena<br>Sativa | Setaria<br>italica | Lolium<br>perenne | Solanum<br>lycopersicum | Sinapis<br>alba | Stellaria<br>media | Phaseolus<br>vulgaris |
| DL<br>CH$_3$CHPO$_2$H$_2$<br>\|<br>NH$_2$ | 4 | 1 | 4 | 2 | 1 | 4 | 1 |

KEY:
9 = plants undamaged (as untreated control)
1 = plants completely dead.
8-2 = intermediate stages of damage.

The compound according to the present invention which was tested exhibited a pronounced contact herbicidal action on some plants and, as a symptom of the growth inhibiting properties, halted the growth of many plants.

USE EXAMPLE 2

Growth inhibition in grasses

Seeds of the grasses *Lolium perenne, Poa pratensis, Festuca ovina* and *Dactylis glomerata* were sown in plastic bowls containing an earth/peat/sand mixture (6:3:1) and were watered normally. Every week the emergent grasses were cut back to a height of 4 cm and, 40 days after being sown and 1 day after the last cutting, were sprayed with aqueous spray liquors of an active compound of the formula I. The amount of active compound corresponded to 2.5 kg of active substance per hectare. The growth of the grasses was evaluated 10 and 21 days after application and the result is given in Table 2.

TABLE 2

| | GROWTH INHIBITION IN GRASSES | | | |
|---|---|---|---|---|
| Plant<br>Compound | Lolium<br>perenne | Poa<br>pratensis | Festuca<br>ovina | Dactylis<br>glomerata |
| DL<br>CH$_3$CHPO$_2$H$_2$<br>\|<br>NH$_2$ | 4 | 3 | 4 | 3 |

KEY:
9 = plants undamaged (as untreated control)
1 = plants completely dead
8-2 = intermediate stages of damage

USE EXAMPLE 3

Growth inhibition in cereals

Spring wheat (*Triticum aestivum*), and spring barley (*Hordeum vulgare*) were sown in sterilised earth in plastic beakers and the plants were grown in a greenhouse. 5 days after being sown, the cereal shoots were treated with a spray liquor of the active compound. The application to the leaves corresponded to 4 kg of the active compound per hectare. Evaluation was carried out after 21 days and the results are given in Table 3.

TABLE 3

| | GROWTH INHIBITION IN CEREALS | |
|---|---|---|
| Plant<br>Compound | Triticum<br>aestivum | Hordeum<br>vulgare |
| DL<br>CH$_3$CHPO$_2$H$_2$<br>\|<br>NH$_2$ | 3 | 2 |

KEY:
9 = plants undamaged (as untreated control)
1 = plants completely dead
8-2 = intermediate stages of damage The active compounds of the formula I cause a noticeable inhibition of growth both in the case of the grasses and in the case of the cereals.

Some active compounds of the formula I which can be used according to the invention and which can constitute the active ingredient of the agent, are listed hereafter. These compounds have been prepared conforming to German OS No. 2,722,162, with the exception of aminomethanephosphonous acid (R=H in formula 1). Reaction of benzhydrylamine and 40% aqueous formaldehyde followed by reaction with hypophosphorous acid and subsequent acid treatment is described in OS No. 2,722,162 gives aminomethane phosphonous acid.

Aminomethanephosphonous acid, m.p. >260°.
DL-1-Aminoethanephosphonous acid, m.p. 223°–224° C. (decomp.).
DL-1-amino-2-methyl-propanephosphonous acid, m.p. 201° C. (dec.).
DL-1-amino-n-butane-phosphonous acid, m.p. 236° C. (dec.).
DL-1-amino-n-pentanephosphonous acid, m.p. 230°–232° C. (dec.).
DL-1-amino-2-methylbutane-phosphonous acid, m.p. 203°–205° C. (dec.).
(−)-1-amino-2-methylpropane-phosphonous acid, m.p. 209° C.; specific rotation $[\alpha]_D^{25} -3,6°$ (1,5% in water).
(−)-1-aminoethanephosphonous acid, m.p. 236,5°–237° C.; $[\alpha]_D^{25} -6°$ (2% in water).
(+)-1-amino-2-methylpropane-phosphonous acid, m.p. 209° C.; $[\alpha]_D^{25} +3,5°$ (1,5% in water).
(+)-1-aminoethane-phosphonous acid, m.p. 233°; $[\alpha]_D^{25} +5,5°$ (2% in water).
DL-1-amino-2-hydroxyethane-phosphonous acid, m.p. 210°.
DL-1-aminopropane-phosphonous acid, m.p. 226°–227° (dec.).
sodium salt of DL-1-aminoethane-phosphonous acid, a transparent glass.
Hydrobromide of DL-1-amino-2-methylpropane-phosphonous acid, m.p. 134°–136° (dec.).

What is claimed is:

1. A method of inhibiting plant growth comprising applying to the sown areas or to the plants an effective plant growth inhibiting amount of a compound of the formula

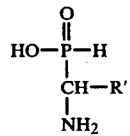

wherein R' is an alkyl group having from 1° to 5° C. atoms which is unsubstituted or substituted by hydroxyl; as well as plant physiologically acceptable salts thereof or optical isomers thereof.

2. A method according to claim 1 wherein the treated plants are monocotyledonous or dicotyledonous plants.

3. A method according to claim 2 wherein the compound is applied as a post-emergent treatment of the plants.

4. A method according to claim 3 wherein the plant is a grass, a cereal crop, tobacco, soya or an ornamental plant.

5. A method according to claim 1 wherein the amount of compound is between 0.1 and 5 kg per hectare for the post-emergent treatment of existing crops.

6. The method of claim 1, wherein R' is unsubstituted, straight chain $C_1$–$C_5$ alkyl.

7. The method of claim 6, wherein R' is methyl.

8. A method for combatting undesirable weeds in crop cultures comprising applying to the area to be treated a herbicidally effective amount of a compound according to claim 1.

9. The method of claim 8, wherein said compound is applied as a post-emergent treatment of the crops.